(12) United States Patent
Drake et al.

(10) Patent No.: US 11,617,600 B2
(45) Date of Patent: *Apr. 4, 2023

(54) APPARATUS FOR FORMING A PASSAGEWAY IN TISSUE AND ASSOCIATED INTERVENTIONAL MEDICAL SYSTEMS

(71) Applicant: Medtronic, Inc., Minneapolis, MN (US)

(72) Inventors: Ronald A. Drake, St. Lous Park, MN (US); Matthew D. Bonner, Plymouth, MN (US); Trent M. Fischer, St. Paul, MN (US); Brian P. Colin, Anoka, MN (US); Lester O. Stener, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 800 days.

This patent is subject to a terminal disclaimer.

(21) Appl. No.: 16/655,898

(22) Filed: Oct. 17, 2019

(65) Prior Publication Data
US 2020/0046407 A1    Feb. 13, 2020

Related U.S. Application Data

(63) Continuation of application No. 15/387,224, filed on Dec. 21, 2016, now Pat. No. 10,448,971.

(51) Int. Cl.
*A61B 17/34* (2006.01)
*A61M 25/06* (2006.01)
(Continued)

(52) U.S. Cl.
CPC .... *A61B 17/3468* (2013.01); *A61B 17/00234* (2013.01); *A61B 17/3478* (2013.01);
(Continued)

(58) Field of Classification Search
CPC .......... A61B 17/3468; A61B 17/3478; A61B 2017/00247; A61N 1/0573; A61N 1/3756; A61M 25/0662
See application file for complete search history.

(56) References Cited

U.S. PATENT DOCUMENTS

| | | |
|---|---|---|
| 5,728,140 A | 3/1998 | Salo et al. |
| 6,517,519 B1 | 2/2003 | Rosen et al. |

(Continued)

FOREIGN PATENT DOCUMENTS

| | | |
|---|---|---|
| CN | 205729432 U | 11/2016 |
| WO | 199107202 A1 | 5/1991 |

(Continued)

OTHER PUBLICATIONS (PCT/US2017/067314) PCT Notification of Transmittal of the International Search Report and the Written Opinion of the International Searching Authority, dated Mar. 21, 2018, 18 pages.
(Continued)

*Primary Examiner* — Martin T Ton
(74) *Attorney, Agent, or Firm* — Shumaker & Sieffert, P.A.

(57) ABSTRACT

An apparatus for forming a passageway through tissue includes a dilator mounted to a shaft, wherein the dilator includes a first portion, which has an increasing taper from a first outer diameter to a larger second outer diameter, and a second portion, which has a decreasing taper from the first portion to a distal end of the dilator, and which includes an external non-cutting thread formed along the decreasing taper. Lumens of the dilator and shaft provide a conduit for means to pierce through the tissue, for example, an elongate wire that includes a piercing tip. In some cases, the dilator first portion is expandable to, and contractible from, the larger second outer diameter, wherein the apparatus may include a spreading member configured to slide between the
(Continued)

shaft and the first portion. The apparatus may be included in a system with an introducer sheath.

9 Claims, 9 Drawing Sheets

(51) Int. Cl.
    *A61N 1/05*     (2006.01)
    *A61N 1/375*     (2006.01)
    *A61M 29/00*     (2006.01)
    *A61B 17/00*     (2006.01)
    *A61N 1/372*     (2006.01)

(52) U.S. Cl.
    CPC ........ *A61M 25/0662* (2013.01); *A61M 29/00* (2013.01); *A61N 1/0573* (2013.01); *A61N 1/3756* (2013.01); *A61B 2017/00247* (2013.01); *A61M 2210/125* (2013.01); *A61N 1/37205* (2013.01)

(56) References Cited

U.S. PATENT DOCUMENTS

| | | |
|---|---|---|
| 6,767,355 B2 | 7/2004 | Frova et al. |
| 7,048,733 B2 | 5/2006 | Hartley et al. |
| 8,509,916 B2 | 8/2013 | Byrd et al. |
| 8,777,841 B2 | 7/2014 | Frassica et al. |
| 8,870,755 B2 | 10/2014 | Frassica et al. |
| 8,942,829 B2 | 1/2015 | Rothstein et al. |
| 10,398,892 B2 | 9/2019 | Anderson et al. |
| 10,448,971 B2 | 10/2019 | Drake et al. |
| 10,751,061 B2 | 8/2020 | Jiang et al. |
| 2004/0064143 A1* | 4/2004 | Hicken ................ A61B 17/885 606/90 |
| 2006/0247642 A1 | 11/2006 | Stone et al. |
| 2007/0088418 A1* | 4/2007 | Jacobson ........... A61N 1/37217 607/116 |
| 2007/0233252 A1 | 10/2007 | Kim |
| 2008/0015569 A1 | 1/2008 | Saadat et al. |
| 2008/0234717 A1* | 9/2008 | Bruszewski .......... A61M 29/00 606/167 |
| 2009/0275972 A1 | 11/2009 | Uemura et al. |
| 2011/0098531 A1 | 4/2011 | To |
| 2011/0264098 A1 | 10/2011 | Cobbs |
| 2012/0172690 A1 | 7/2012 | Anderson et al. |
| 2012/0239069 A1 | 9/2012 | Benscoter et al. |
| 2012/0259263 A1 | 10/2012 | Celermajer et al. |
| 2013/0116614 A1 | 5/2013 | Ward et al. |
| 2013/0253344 A1* | 9/2013 | Griswold ........... A61N 1/37247 604/95.01 |
| 2015/0094466 A1 | 4/2015 | Moriarty |
| 2015/0094668 A1 | 4/2015 | Wood et al. |
| 2016/0157886 A1 | 6/2016 | WasDyke et al. |
| 2016/0228713 A1* | 8/2016 | Bar-Cohen ............. A61N 1/059 |

FOREIGN PATENT DOCUMENTS

| | | | |
|---|---|---|---|
| WO | 200222206 A1 | 3/2002 | |
| WO | 2008115924 A2 | 9/2008 | |
| WO | 2012109557 A2 | 8/2012 | |
| WO | 2016018434 A1 | 2/2016 | |
| WO | WO-2016018434 A1 * | 2/2016 | ......... A61B 17/3423 |

OTHER PUBLICATIONS

First Office Action and Search Report, and translation thereof, from counterpart Chinese Application No. 201780076710.4 dated Nov. 23, 2021, 16 pp.

Decision on Rejection and translation thereof, from Chinese Application No. 201780076710.4 dated Jun. 8, 2022, 12 pp.

Prosecution History from U.S. Appl. No. 15/387,224, dated Jan. 28, 2019 through Jun. 10, 2019, 41 pp.

Second Office Action, and translation thereof, from counterpart Chinese Patent Application No. 201780076710.4 dated Mar. 25, 2022, 15 pp.

* cited by examiner

APPARATUS FOR FORMING A PASSAGEWAY IN TISSUE AND ASSOCIATED INTERVENTIONAL MEDICAL SYSTEMS

FIELD OF THE INVENTION

The present invention pertains to forming a passageway through tissue in a body of a patient, for example, to position an interventional medical system.

BACKGROUND

Forming a passageway through tissue may be necessary in order to position an interventional medical system for delivery of therapy or diagnostics within an organ or the circulatory system of a patient. Typically, the passageway is formed, via an apparatus that includes a needle, dilator, and introducer sheath, such as is known to those skilled in the art of interventional medical systems. Although a variety of configurations for this type of apparatus are known in the art, there is still a need for new configurations, for example, new configurations that are useful in forming a passageway that facilitates the delivery of an implantable cardiac pacing device.

SUMMARY

Embodiments of an apparatus disclosed herein, for forming a passageway through tissue in a body of a patient, include a relatively flexible elongate shaft and a dilator mounted to a distal end thereof, wherein a first portion of the dilator has an increasing taper from a first outer diameter, at a proximal end of the dilator, to a larger second outer diameter, in proximity to a second portion of the dilator, and the second portion of the dilator has a decreasing taper from the first portion to a distal end of the dilator, and includes an external non-cutting thread formed along the decreasing taper. In some cases, the first portion of the dilator may also include an external non-cutting thread, which is formed along the increasing taper. The dilator further includes a longitudinally extending lumen that extends proximally from a distal opening thereof, located at the distal end of the dilator, wherein the lumen of the dilator is in fluid communication with a lumen of the shaft so that the lumens of the shaft and dilator can provide a conduit for a means to pierce through the tissue, which is delivered out through the distal opening of the dilator lumen. According to some embodiments, the apparatus includes a wire having a piercing distal tip as the means for piercing through the tissue, wherein the wire may include a flexible distal segment having a preformed J-shape.

In some embodiments of an interventional medical system that includes an introducer sheath and the aforementioned apparatus, wherein a lumen of the introducer sheath is sized to receive passage of the apparatus therethrough, the first portion of the apparatus dilator is configured to expand to, and contract from, the larger second outer diameter, for example, via another member of the apparatus. Thus, the larger second outer diameter of the apparatus may be greater than or equal to an outer diameter of the introducer sheath, after the dilator is passed out from the lumen of the introducer sheath. The other member of the apparatus, according to some embodiments, may be a spreading member configured to slide within the first portion of the dilator, between the shaft and the first portion.

According to some embodiments, an interventional medical system includes a relatively compact implantable medical device, an introducer sheath, and any of the aforementioned embodiments of the apparatus, wherein the apparatus and the introducer sheath can be used to form a passageway through an interatrial septum of a patient's heart for subsequent delivery of the medical device therethrough, via the sheath. Although embodiments of the apparatus are described in the context of embodiments of such a system, use of the apparatus in other contexts is not outside the scope of the present invention. For example, some other contexts include forming a passageway from an epidermal site and through underlying tissue to a pericardial space, or to a vein of the patient.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
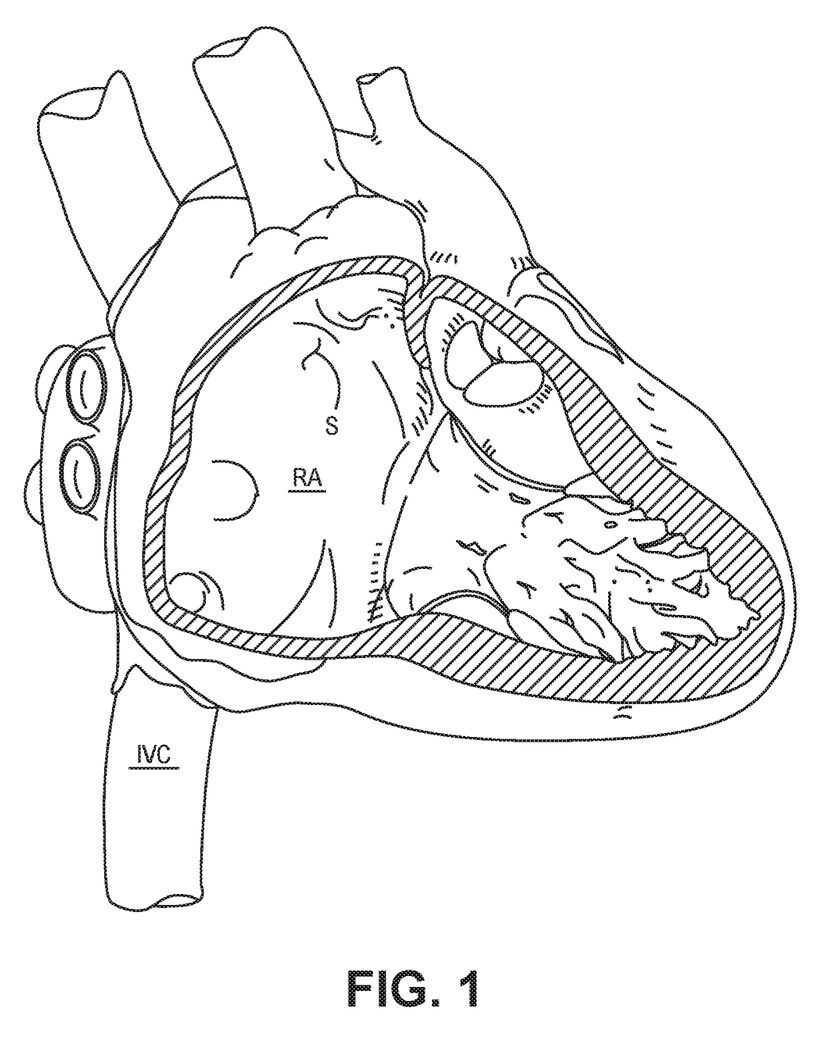
FIG. 1 is a schematic diagram showing a potential site for forming a passageway through tissue via embodiments of an apparatus.
Figure 2A:
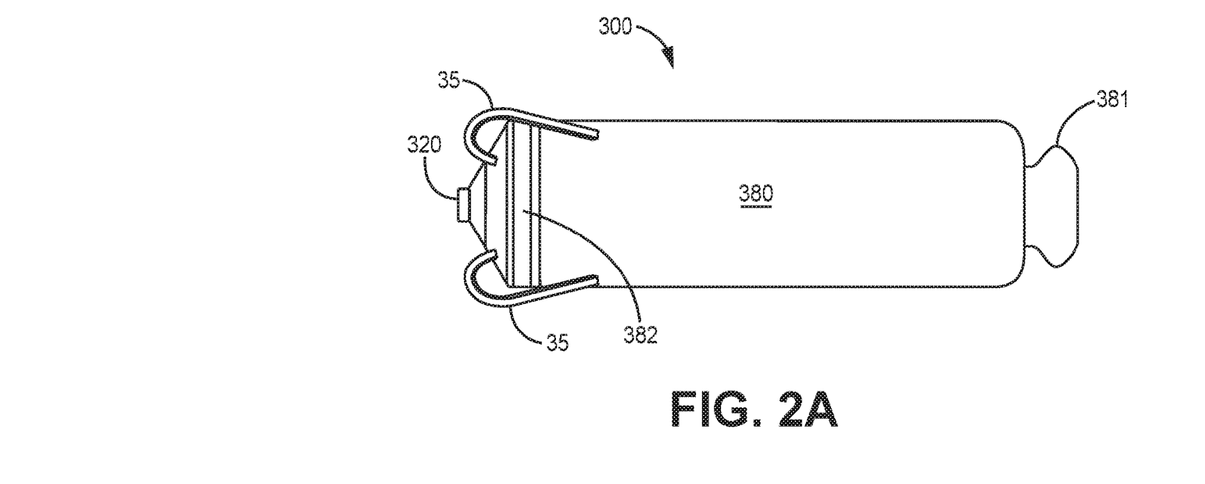
FIG. 2A is a plan view of an exemplary relatively compact implantable medical device that may be included in systems of the present invention, according to some embodiments.

FIG. 1 is a schematic diagram showing a potential site S for forming a passageway through the interatrial septum so that a relatively compact implantable medical device, such as device 300 shown in FIG. 2A, may be delivered to a cardiac implant site on a left side of a patient's heart. Site S is preferably located along the septum in proximity to the Fossa Ovalis. FIG. 2A is a plan view of device 300, which is wholly contained within a relatively compact package, the entirety of which is configured for implant in close proximity to a pacing site. Device 300 may be included in systems of the present invention, according to some embodiments, which also include a delivery tool that is described in the commonly assigned United States Patent Application US 2015/0094668.

FIG. 2A illustrates medical device 300 including a hermetically sealed housing 380, which extends from a proximal end 381 thereof to a distal end 382 thereof, and an electrode 320, which is mounted to housing distal end 382. According to the illustrated embodiment, an electronic controller (not shown), for example, a pulse generator and an associated power supply, are contained within housing 380, and electrode 320 is electrically coupled to the controller via a hermetically sealed feedthrough assembly (not shown) such as is known in the art. Device housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing.

Device 300 further includes a fixation member, for example, formed by a plurality of super-elastic fingers 35 spaced apart from one another around a perimeter of housing distal end 382, which are configured to secure electrode 320 in intimate tissue contact at an implant site. Although only two fixation fingers 35 are shown in FIG. 3A, device 300 may include as many as eight. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation fingers 35 may be mounted to distal end 382 of device housing 380, for example, in a manner similar to that described for a fixation component 102 in a commonly assigned United States Patent Application 2012/0172690, which description is hereby incorporated by reference. The super-elastic nature of Nitinol allows fingers 35 to elastically deform between a relaxed condition, which is shown, and an extended condition, in which a free end of each finger extends distally away from distal end 382 of device housing 380, for example, when device 300 is loaded into the aforementioned delivery tool, which is described in the commonly assigned United States Patent Application US 2015/0094668, and which is shown, in FIG. 2B, extending within a lumen of an introducer sheath 200, being designated with reference numeral 100.

Figure 2B:
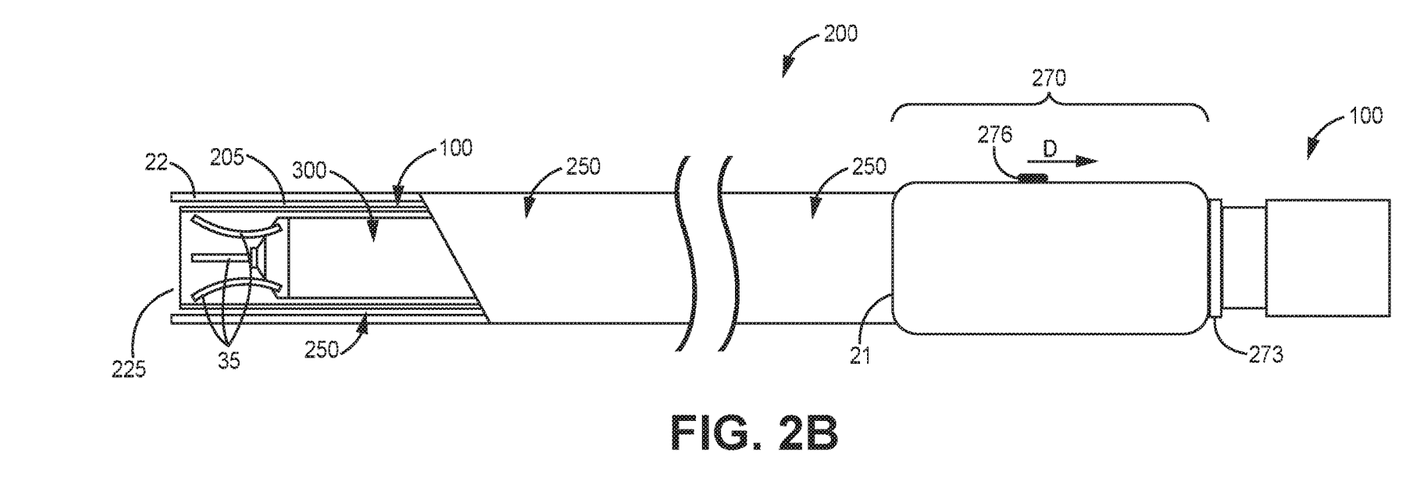
FIG. 2B is a plan view, which includes a partial cross-section, of a portion of an exemplary interventional medical system.
Figure 3A:
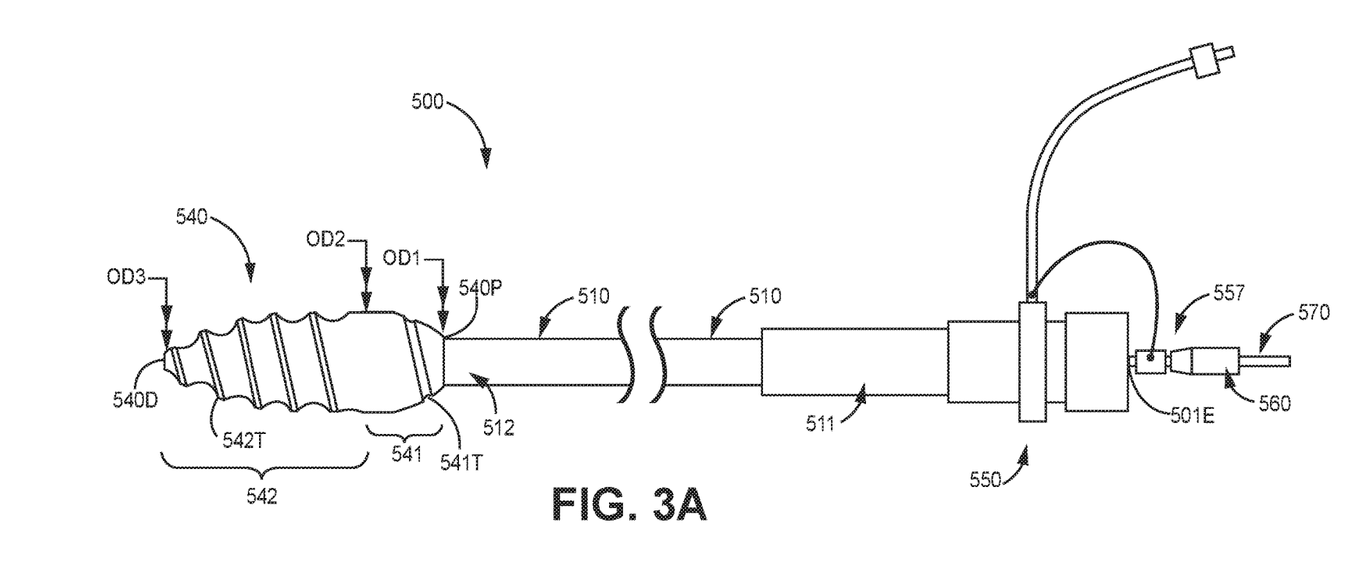
FIG. 3A is a plan view of an apparatus for forming a passageway through tissue in a body of a patient, according to some embodiments.

FIG. 2B is a plan view, with a partial cross-section, of a portion of an exemplary interventional medical system, which includes device 300, delivery tool 100, and introducer sheath 200. FIG. 2B illustrates sheath 200 including an elongate tubular member 250 and a handle assembly 270 coupled to a proximal end 21 of member 250, wherein tubular member 250 defines a lumen 205, which is in fluid communication with a proximal port opening 273 of handle assembly 270, and is sized to allow passage of tool 100, with device 300 loaded therein, therethrough. FIG. 2B further illustrates a distal end 22 of tubular member 250 defining a distal-most opening 225 of lumen 205, which allows deployment of device 300 therethrough to an implant site. According to some embodiments, device 300 may be directly loaded into sheath lumen 205 without the need for delivery tool 100. With reference back to FIG. 1, to access an implant site located on the left side of a patient's heart, for example, within the left ventricle (not seen), after positioning sheath 200 in the patient's right atrium RA, for example, via the inferior vena cava IVO from a femoral access site, an operator will need to pass sheath distal end 22 through tissue that forms the interatrial septum for example, at site S. Thus, for forming a passageway through the tissue, the system of FIG. 2B may also include an apparatus 500 (described below in conjunction with FIGS. 3A-B), or an apparatus 600 (described below in conjunction with FIGS. 6A-B, 7A-B).

Before turning to FIG. 3A, with further reference to FIG. 2B, handle assembly 270 of introducer sheath 200 is shown including a control member 276 for an optional steering assembly of sheath 200. The steering assembly, according to configurations known in the art, may further include a pull band mounted on tubular member 250, in proximity to sheath distal end 22, and an elongate pull wire that extends along a length of tubular member 250, being coupled to the pull band and to control member 276. Moving control member 276, per arrow D, causes the pull wire to deflect outer tubular member 250, which may be useful in navigating the system. Alternately, tubular member 250 of sheath 200 may include a pre-formed curvature, in proximity to distal end 22, which is useful in navigating the system.

Figure 3B:
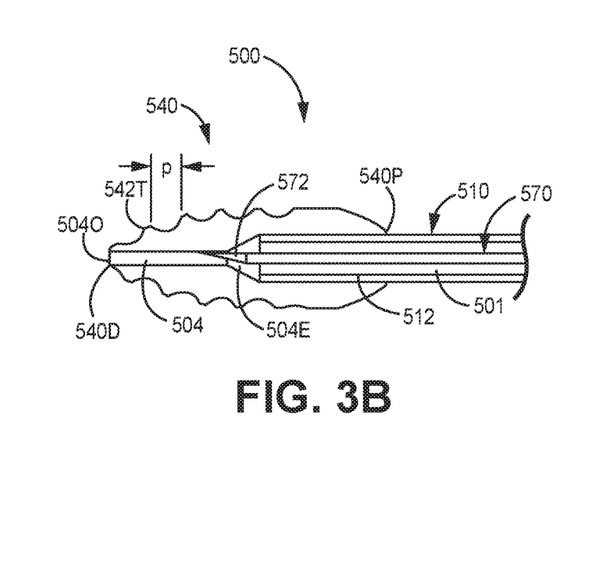
FIG. 3B is a longitudinal cross-section view through a portion of the apparatus, according to some embodiments.

FIG. 3A is a plan view of apparatus 500, according to some embodiments; and FIG. 3B is a longitudinal cross-section view through a portion of apparatus 500, according to some embodiments. FIGS. 3A-B illustrate apparatus 500 including a relatively flexible elongate shaft 510 and a relatively rigid dilator 540 mounted thereto, wherein a first portion 541 of dilator 540 extends around a distal end 512 of shaft 510, and a second portion 542 of dilator 540 extends from first portion 541 to a distal end 540D of dilator 540. Dilator first portion 541 is shown having an increasing taper from a first outer diameter OD1 (e.g., about 0.12 inch), at a proximal end 540P of dilator 540, to a larger second outer diameter OD2 (e.g., about 0.3 inch), in proximity to second portion 542 dilator 540; and dilator second portion 542 is shown having a decreasing taper from second outer diameter OD2 to a smaller third outer diameter OD3 (e.g., about 0.04 inch), in proximity to distal end 540D of dilator 540. FIG. 3A further illustrates dilator second portion 542 including an external non-cutting thread 542T (e.g., having a radiused crest) formed along the decreasing taper. A pitch p of thread 542T (FIG. 3B) may be about 0.125 inch in some embodiments. With reference back to FIG. 2B, according to some embodiments, larger second outer diameter OD2 of dilator 540 makes nearly a line-to-line fit of dilator 540 within lumen 205 of introducer sheath 200, so that apparatus 500, when passed through introducer sheath 200 and out through distal-most opening 225, for example, as described below in conjunction with FIGS. 5A-D, can form a passageway through the tissue of the largest possible size for sheath distal end 22 to pass through the tissue.

According to the illustrated embodiment, an operator, by engaging dilator distal end 540D with the tissue, at an opening previously formed therethrough, and then rotating dilator 540 around a longitudinal axis thereof, causes dilator 540 to advance through the opening as a graduating diameter of non-cutting thread 542T (graduating from smaller third outer diameter OD3 to larger second outer diameter OD2) gradually increases the size of the opening to create, without undue trauma, the passageway for sheath distal end 22 to pass through the tissue. The increasing taper of dilator first portion 541 facilitates retraction of dilator 540 back through the passageway, for example, since the tissue may have a relative toughness and elasticity to cause some contraction of the formed passageway. As dilator 540 is retracted, the operator may simultaneously push sheath 200 to advance distal end 22 over dilator 540 and through the passageway. According to some embodiments, as shown in FIG. 3A, dilator first portion 541 also includes an external non-cutting thread 541T formed along the increasing taper, to further facilitate retraction of dilator 540 back through the passageway, via rotation thereof around the longitudinal axis.

With reference to FIG. 3B, according to some embodiments of apparatus 500, shaft 510 and dilator 540 include lumens 501, 504, respectively, which are in fluid communication with one another to provide a conduit for a means to pierce through the tissue, wherein the piercing forms the aforementioned opening that is a precursor to the passageway formed by dilator 540. The means for piercing may be mechanical, as described below, or via radiofrequency energy, such as delivered through a wire like the Baylis Medical radiofrequency NRG® Transseptal Needle.

FIG. 3B illustrates the means to pierce through the tissue being an elongate wire 570 that includes a piercing distal tip 572, which is slideably engaged within lumens 501, 504. FIG. 3B further illustrates dilator lumen 504 having a nominal diameter that is smaller than that of shaft lumen 501, for example, for a 'snugger' fit around wire 570, just proximal to wire distal tip 572, that can provide enhanced back-up support for tip 572, when the operator advances tip 572 out through a distal opening 504O of lumen 504 to pierce through the tissue. Thus, dilator lumen 504 is shown extending distally from a funnel-shaped entry 504E that increases an ease of passing wire distal tip 572 from shaft lumen 501 to dilator lumen 504. Wire 570, after having been passed out though distal opening 504O, to pierce through the tissue, can form a rail to guide dilator 540 as the operator rotates dilator 540 to create the passageway through the tissue, as described below.

With reference back to FIG. 3A, a proximal end of wire 570 extends out from a proximal hub 550 of apparatus 500, and has a tool 560 attached thereto, for example, to facilitate the operator's handling of wire 570. Proximal hub 550, which is shown joined to a strain-relieved proximal end 511 of shaft 510, may be formed by a Tuohy-Borst type fitting with a side-port known to those skilled in the art. FIG. 3A further illustrates an insertion stop 557, for example, being formed by a polymer tube, fitted around the proximal end of wire 570, between hub 550 and tool 560, so that tool 560 will abut stop 557 to prevent wire 570 from sliding distally in lumens 501, 504 before the operator is ready to pierce through the tissue. After the operator has positioned distal end 540D of dilator 540 adjacent the tissue, the operator can remove insertion stop 557 from wire 557; and, as illustrated in FIG. 3A, insertion stop 557 may be tethered proximal end 511 of shaft 510, for example, to hub 550, so the operator cannot misplace it.

According to an exemplary embodiment, shaft 510, which may have a nominal outer diameter of about 0.12 inch and extend over a length of up to approximately 100 cm, from proximal end 511 to distal end 512, is formed by a stainless steel braid-reinforced medical grade polymer, for example, one or more appropriate grades of polyether block amide, which are arranged for decreasing stiffness from proximal end 511 to distal end 512 (e.g., including PEBAX® 3533, 4033, 6333, and 7233), and has a fluoropolymer (e.g., PTFE) or a polyether block amide material lining lumen 501. A length of dilator 540, from proximal end 540P to distal end 540D may be up to about 1 inch (2.5 cm). Dilator 540, for example, formed from a relatively rigid medical grade plastic that has a relatively low surface friction (e.g., polyoxymethylene or polyamide), may be over-molded onto shaft distal end 512, or machined or molded as a separate component 540-C, for example, as shown in FIGS. 4A-B, which is then secured to shaft distal end 512.

Figure 4A:
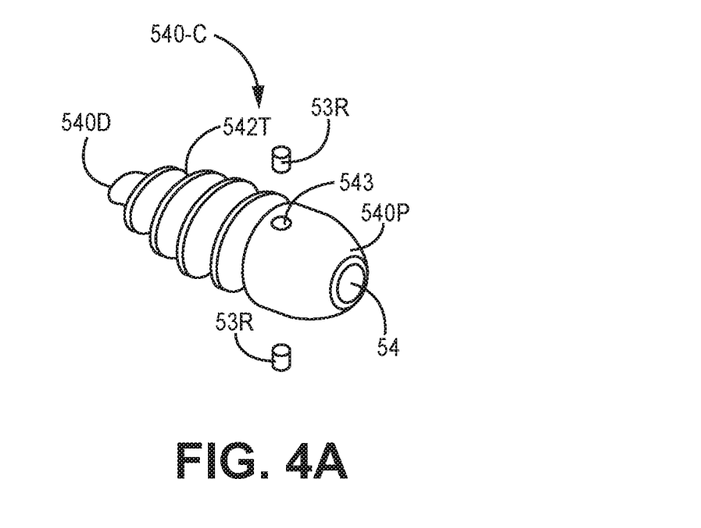
FIG. 4A is an exploded perspective view of a dilator component, according to some embodiments.
Figure 4B:
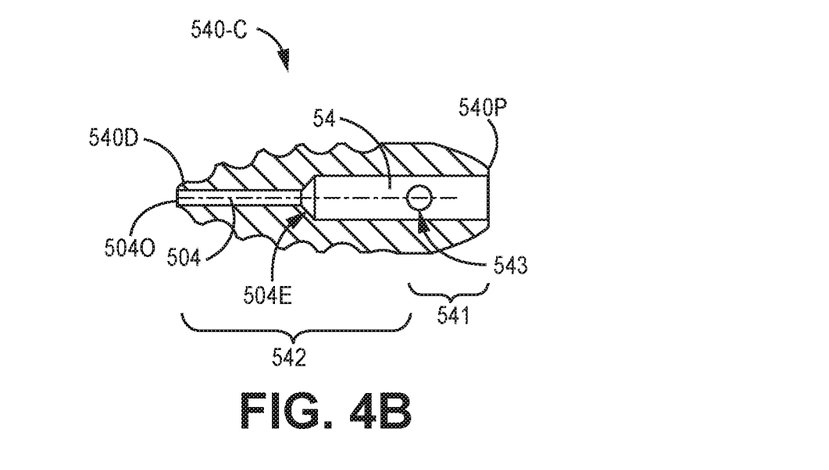
FIG. 4B is a longitudinal cross-section view of the component, according to some embodiments.

FIG. 4A is an exploded perspective view of dilator component 540-C, according to some embodiments; and FIG. 4B is a longitudinal cross-section view of component 540-C, according to some embodiments. FIGS. 4A-B illustrate component 540-C including a mounting bore 54 that extends from proximal end 540P, along first portion 541 and into second portion 542, for example, over a length of about 0.5 inch. FIG. 4B further illustrates bore 54 extending to funnel-shaped entry 504E of lumen 504 so that bore 54 is in fluid communication therewith. According to the illustrated embodiment, bore 54 is sized to allow insertion of shaft distal end 512 therein for mounting of dilator 540 thereto, so that shaft lumen 501 is in fluid communication with dilator lumen 504. A hole 543 is shown formed through a sidewall of dilator first portion 541, wherein hole 543 may extend from an outer surface of first portion 541 to bore 54, and then back through an opposing sidewall of first portion 541, to the outer surface on the opposite side of bore 54. According to some constructions of apparatus 500, hole 543 may serve as a pilot hole to form a hole (not shown) through shaft distal end 512 when inserted in bore 54, and then the aligned holes on either side of shaft lumen 501 may be filled with a material, for example, a medical grade adhesive, that provides a mechanical interlocking between dilator component 540-C and shaft 510. With further reference to FIG. 4A, dilator component 540-C further includes a pair of radiopaque markers 53R, each of which is fitted into a corresponding hole 543, according to some embodiments. Dilator component 540-C may be machined from a relatively rigid medical grade thermoplastic (e.g., Delrin®, a polyoxymethylene copolymer), and markers 53R may be tubular bands of 90/10 Platinum/Iridium.

Figure 5A:
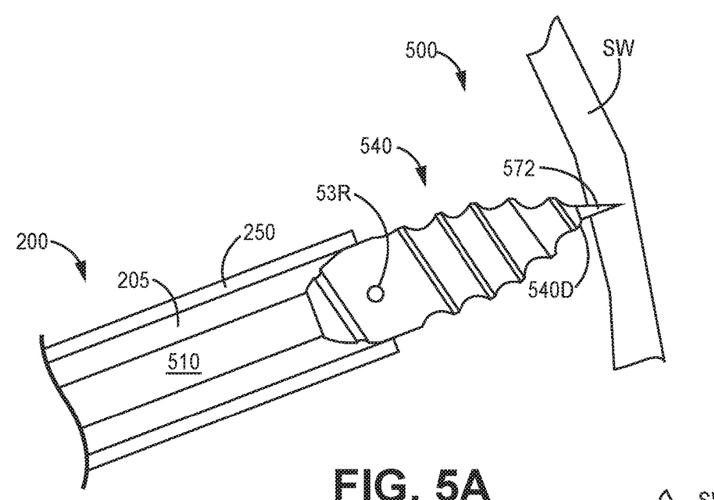
FIGS. 5A-D are schematics depicting a method for forming the passageway through the tissue.
Figure 5B:
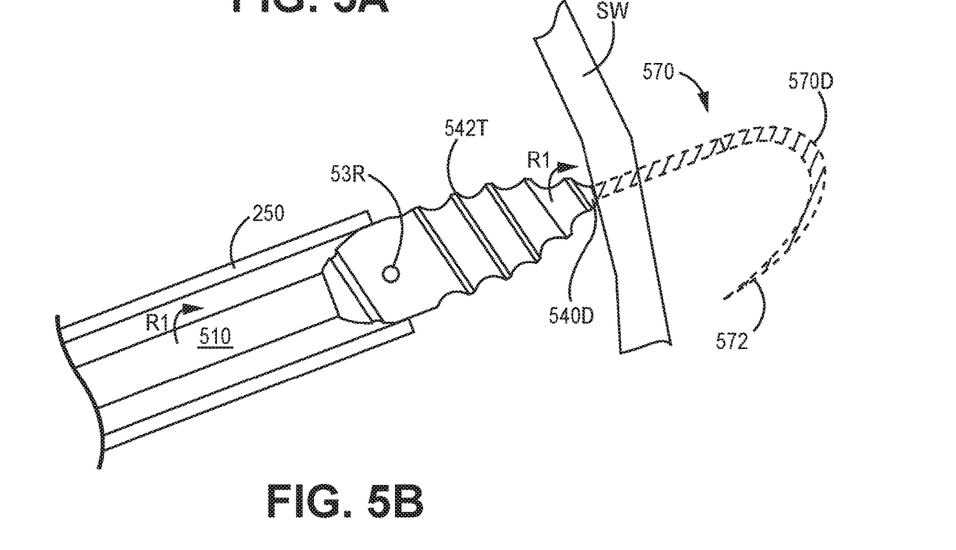
Figure 5C:
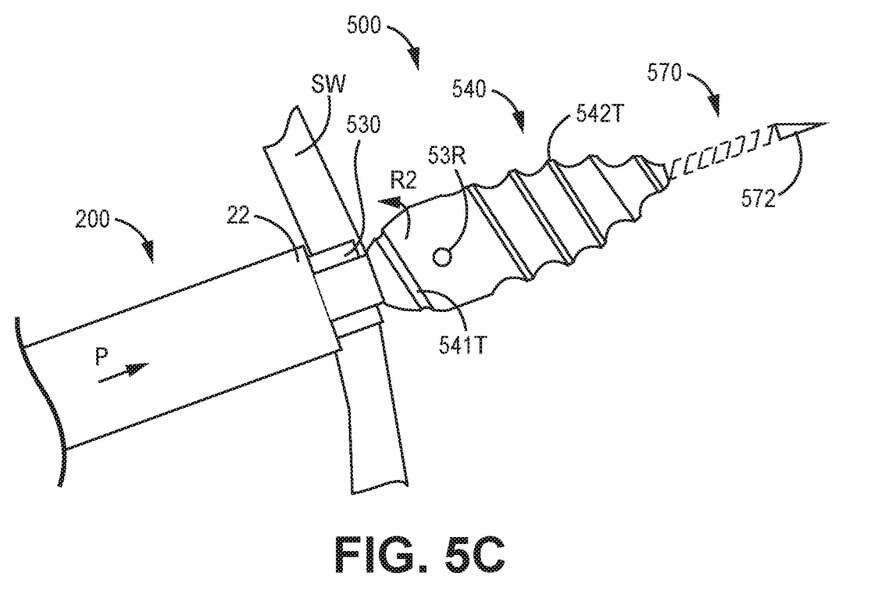
Figure 5D:
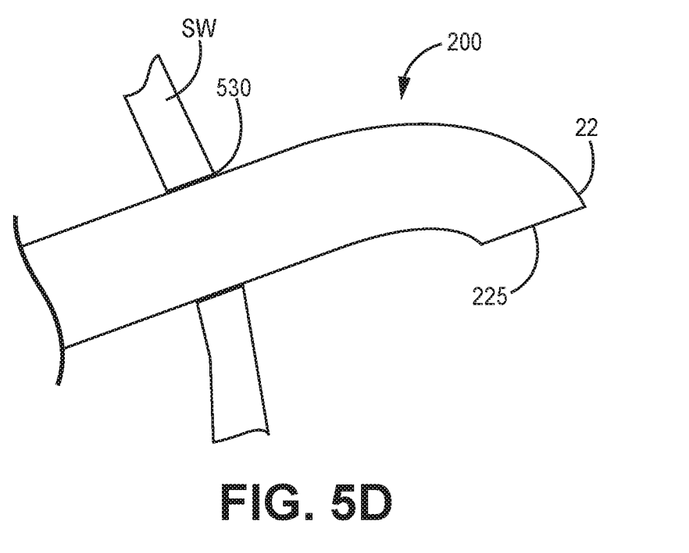

FIGS. 5A-D are schematics depicting a method for forming a passageway 530 through tissue that forms a septal wall SW, for example, the aforementioned interatrial septal wall. FIG. 5A illustrates apparatus 500 having been advanced by an operator into a body of a patient, for example, through sheath lumen 205, until dilator distal end 540D is adjacent to wall SW. FIG. 5A further illustrates piercing distal tip 572 of wire 570 having been advanced by the operator out though dilator lumen distal opening 504O (FIG. 3B) to pierce tissue of septal wall SW. Then, with reference to FIG. 5B, the operator may further advance wire 570 so that tip 572 pierces through wall SW to create an opening therethrough. FIG. 5B illustrates a significantly flexible distal segment 570D of wire 570 having a pre-formed J-shape and extending proximally from piercing distal tip 572. According to the illustrated embodiment, flexible distal segment 570D is deformable to extend lengthwise within lumens 501, 504 (FIG. 3B), and then flops over, after tip 572 pierces through wall SW, to prevent tip 572 from piercing into any other tissue. According to an exemplary embodiment, wire 570 may be a 0.035 inch J Tip Fixed core angiographic guide wire, such as is known to those skilled in the art, and piercing tip 572 (e.g., formed from a medical grade stainless steel hypo-tube) is attached thereto, for example, by crimping and/or welding methods known in the art. With reference to FIGS. 5B-C, after the opening through the tissue of wall SW is formed with wire tip 572, the operator can enlarge the opening to form passageway 530 (FIG. 5C) by rotating shaft 510 and, thus, dilator 540, per arrow R1, which advances dilator 540 through the opening and over wire 570. FIGS. 5A-C further illustrate dilator 540 including radiopaque markers 53R, for example, as described above in conjunction with FIG. 4A, which allow the operator to visualize, via fluoroscopy, the rotation of dilator 540. As described above, the graduated non-cutting thread 542T of dilator creates passageway 530 without undue trauma to septal wall SW. The aforementioned nearly line-to-line fit of dilator 540 within sheath lumen 205, as illustrated in FIG. 5A, provides for the largest possible size of passageway 530 for sheath distal end 22 to pass through. However, as illustrated in FIG. 5C, after passageway 530 is formed, the tissue of septal wall SW may contract somewhat in the wake of dilator 540 due to the aforementioned relative toughness and elasticity of the tissue. Thus, to stretch passageway 530 for sheath distal end 22, the operator may retract dilator 540 through passageway 530 while pushing sheath 200, per arrow P, through passageway 530. The operator may find retraction of dilator 540 difficult by simply pulling apparatus 500, so, embodiments of dilator 540 that include the optional first portion non-cutting thread 541T, as shown, allow the operator to rotate apparatus 500, per arrow R2, to drive a more effective retraction of dilator 540 back through passageway 530. Once the operator has passed sheath distal end 22 through passageway 530, as shown in FIG. 5D, the operator may deflect sheath 200, for example, via the optional steering assembly described above, for example, to orient distal-most opening 225 of sheath 200 toward the left ventricle for a subsequent deployment of device 300, for example, via tool 100 (FIG. 2B) advanced through sheath 200.

Figure 6A:
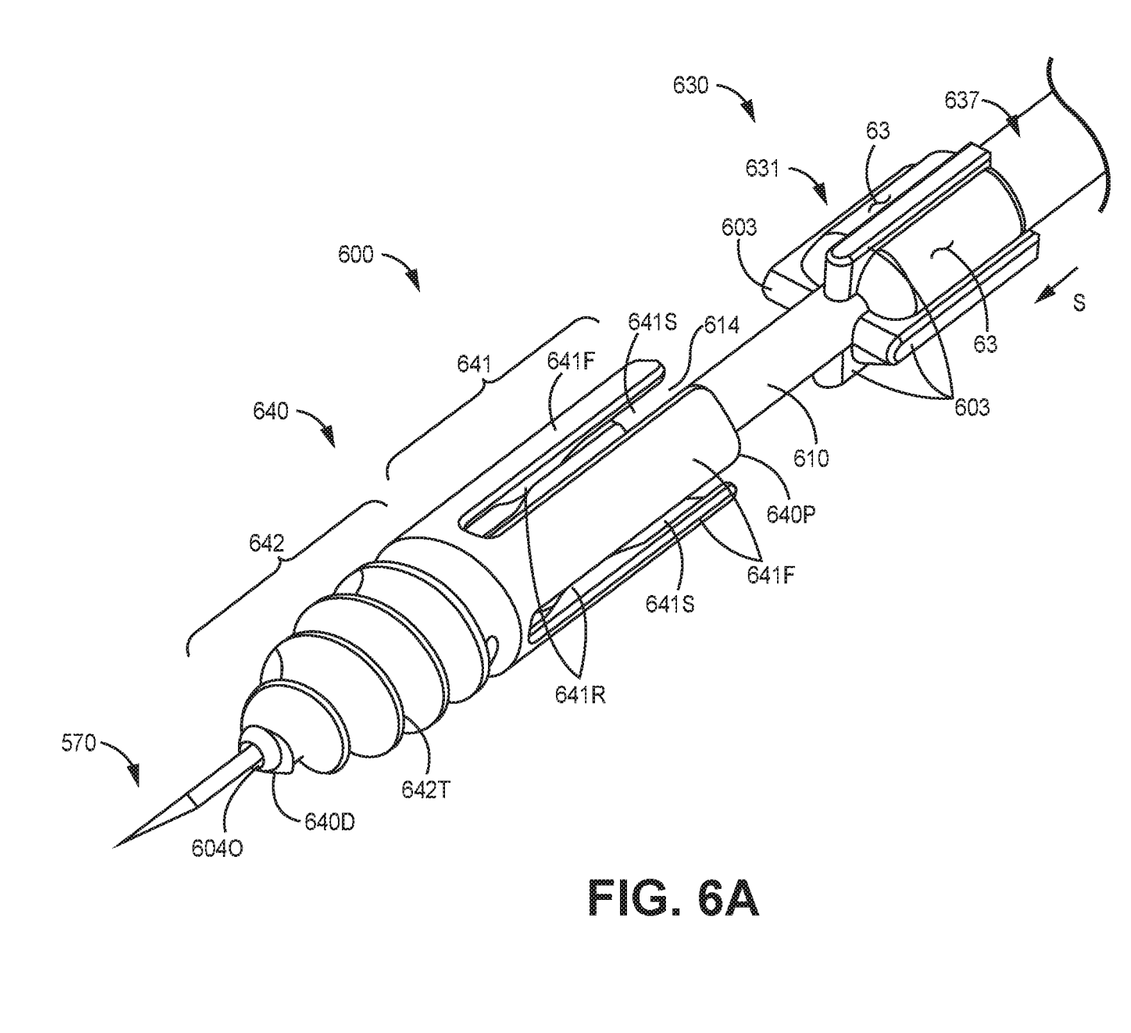
FIGS. 6A-B are perspective views of an alternate embodiment of an apparatus for forming a passageway through tissue in a body of a patient.
Figure 6B:
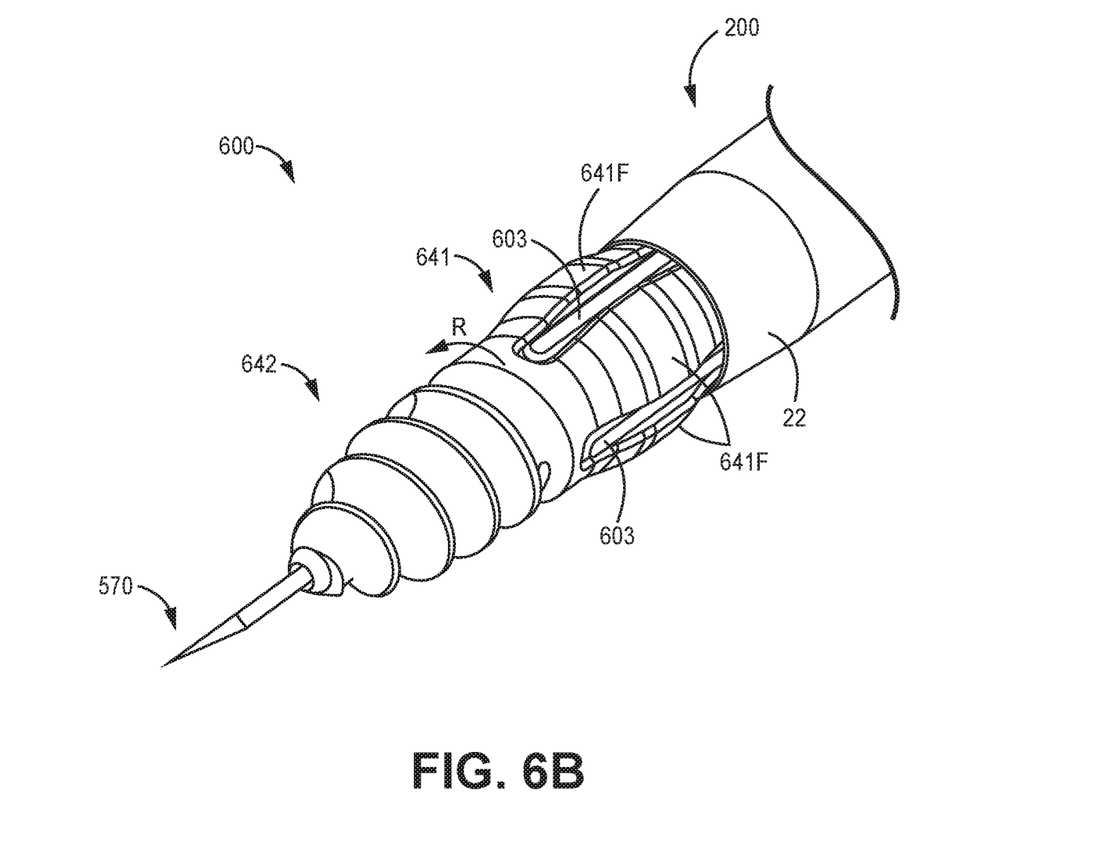
Figure 7A:
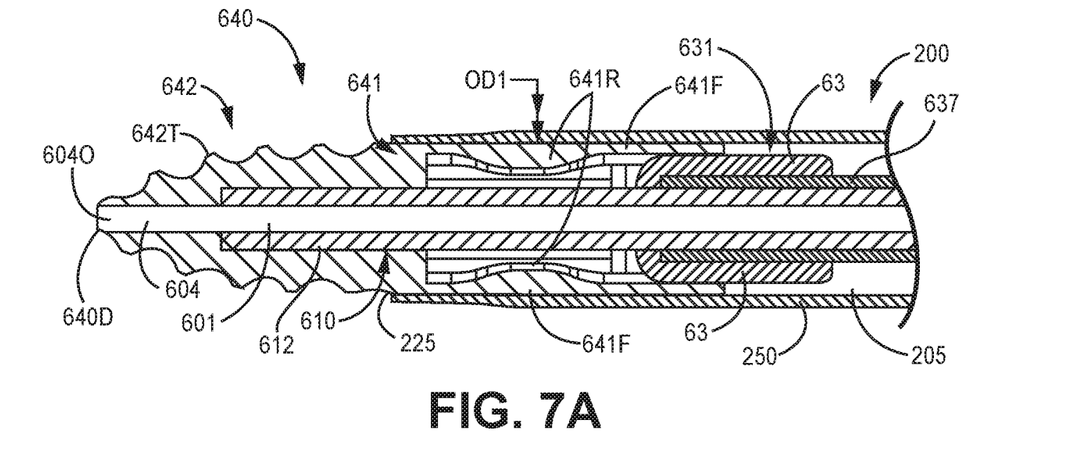
FIGS. 7A-B are cross-section views of the apparatus of FIGS. 6A-B and an introducer sheath, according to some embodiments of an interventional medical system.
Figure 7B:
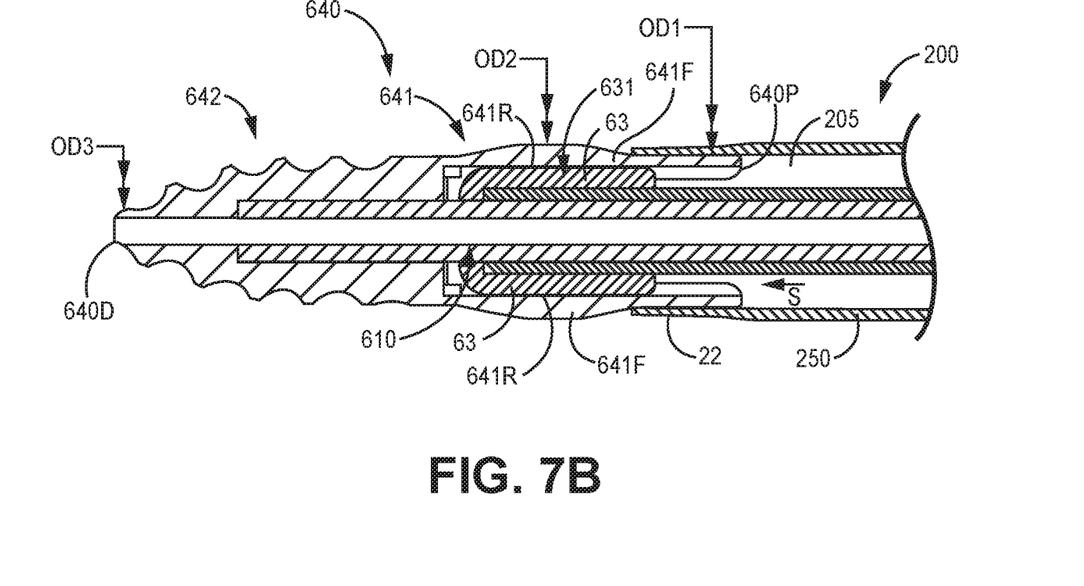

According to some alternate embodiments, an apparatus for forming a passageway through tissue in a body of a patient includes a dilator configured to expand and contract, so that, when expanded, the dilator can form a larger passageway for sheath distal end 22, for example, like a dilator 640 of apparatus 600, which is shown in the perspective views of FIGS. 6A-B. FIG. 6A illustrates dilator 640 mounted to a relatively flexible elongate shaft 610, and the above-described wire 570 extending out from a distal opening 604O of a lumen 604 of dilator (FIGS. 7A-B). Dilator 640 extends from a proximal end 640P to a distal end 640D thereof, and includes a first portion 641 and a second portion 642, wherein second portion 642 has a decreasing taper from first portion 641 to distal end 640D and includes a non-cutting thread 642T (e.g., having a radiused crest) formed along the decreasing taper, similar to second portion 542 of dilator 540. A pitch of thread 642T may be about 0.125 inch, in some embodiments, and outer diameter OD3 (FIG. 7B) of dilator 640, in proximity to distal end 640D, may be about 0.04 inch. According to the illustrated embodiment, dilator second portion 642 is relatively rigid to advance through an opening in tissue, for example, having been formed by wire 570, and to gradually increase the size of the opening with the graduated thread 642T, which creates, without undue trauma, the passageway, as apparatus 600 is rotated per arrow R (FIG. 6B). As was described above for dilator 540, lumen 604 of dilator 640 is in fluid communication with a lumen 601 of shaft 610 (FIGS. 7A-B) to provide a conduit for a means to pierce through the tissue, for example, wire 570.

FIG. 6A further illustrates apparatus 600 including a spreading member 630, which extends around shaft 610 in sliding engagement therewith, for the purpose of expanding dilator first portion 641, as shown in FIGS. 6B and 7B, and described in detail below. In FIG. 6A, spreading member 630 is shown including an elongate tube 637 and a spreading head 631 mounted thereto. According to the illustrated embodiment, an operator can slide spreading member 630 distally, by pushing tube 637, per arrow S, to move spreader head 631 into a gap 614 that extends between dilator first portion 641 and shaft 610, for example, as illustrated in the cross-section views of FIGS. 7A-B. With further reference to FIGS. 6A-B, dilator first portion 641 is expandable by means of a plurality of flaps 641F that extend proximally from second portion 642 to free ends thereof at proximal end 640P of dilator 640. FIG. 6A shows flaps 641F being spaced apart from one another, around a circumferential perimeter of first portion 641, by a plurality of slots 641S. Each flap 641F includes an internal ridge 641R, so that when the operator slides spreader head 631 into gap 614, between dilator first portion 641 and shaft 610, each of a plurality of engagement surfaces 63 of head 631 confronts a corresponding ridge 641R to push the corresponding flap 641F of dilator first portion 641 outward, for example, to larger second outer diameter OD2, as shown in FIG. 6B and FIG. 7B. FIGS. 6A-B further illustrate spreader head 631 including a plurality of longitudinally extending lobes 603, which are spaced apart from one another around a circumferential perimeter of head 631, and are sized to fit within slots 641S of dilator first portion 631, for example, to enhance a rigidity of dilator first portion 641, as dilator 640 is rotated, per arrow R, to advance through the opening and form the passageway.

FIGS. 7A-B are cross-section views of the apparatus 600 and introducer sheath 200, according to some embodiments of an interventional medical system. FIG. 7A illustrates spreader head 63 located between first portion flaps 641F and shaft 610, but proximal to ridges 641R, so that dilator first portion 641 is approximately isodiametric, for example, at first outer diameter OD1, and fits within lumen 205 of introducer sheath 200 for passage therethrough. FIG. 7B illustrates spreader head 631 having been slid in between dilator first portion 641 and shaft 610 so that engagement surfaces 63 confront ridges 641R and expand dilator first portion 641. Thus, the expanded dilator first portion 641 has an increasing taper from first outer diameter OD1, in proximity to dilator proximal end 640P, to larger second outer diameter OD2, in proximity to dilator second portion 642. According to the illustrated embodiment, larger second outer diameter OD2 for dilator 640 is greater than or equal to an outer diameter of introducer sheath 200, at distal end 22, in proximity to distal opening 225 of sheath lumen 205.

According to some methods, the operator may advance apparatus 600, with dilator first portion 641 contracted from second outer diameter OD2, through lumen 205 of introducer sheath 200 until dilator distal end 640D is adjacent to tissue in a patient's body, for example, septal wall SW described above. Then, after the operator forms an opening through the tissue, for example, by advancing wire 570 through apparatus lumens 601, 604 and out distal opening 604O to pierce through the tissue, the operator may rotate apparatus 600 to begin advancing dilator 640 through the opening, either before or after sliding head 631 of spreading member 630 into dilator first portion 641, per arrow S (FIG. 7B), to expand first portion 641 to second outer diameter OD2. As described above, the graduated thread 642T of dilator second portion 642 gradually increases the size of the opening as dilator 640 moves therethrough, and the larger second outer diameter OD2 of dilator first portion 641 makes the passageway, formed from the opening, large enough for the operator to pass sheath distal end 22 therethrough in the wake of dilator 640.

According to an exemplary embodiment, apparatus shaft 610, which may have a nominal outer diameter of about 0.12 inch and extend over a length of up to approximately 100 cm, is formed by a stainless steel braid-reinforced medical grade polymer, for example, one or more appropriate grades of polyether block amide, which are arranged for decreasing stiffness, from a proximal end to a distal end thereof (e.g., including PEBAX® 3533, 4033, 6333, and 7233), and has a fluoropolymer (e.g., PTFE) or a polyether block amide material lining lumen 601. A length of dilator 640, from proximal end 640P to distal end 640D may be up to about 1.5 inch (3.8 cm). Dilator 640, for example, formed from a relatively rigid medical grade plastic that has a relatively low surface friction (e.g., polyoxymethylene or polyamide), may be over-molded onto shaft 610, or machined or molded as a separate component, which is then secured to shaft 610. The same or a similar material may form spreader head 631 of spreading member 630. Spreading member tube 637 may be relatively flexible, for example, being formed from PEBAX® 5533, or relatively stiff, for example, being formed from a suitable medical grade polyimide. If the latter, tube 637, when spreader head 631 is slid within dilator first portion 641, can provide some additional rigidity helpful to advance dilator 640 through the opening to form passageway, and/or, in some cases, to straighten an optional preformed curvature of sheath tubular member 250.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising:
an introducer sheath and an apparatus for forming a passageway through tissue in a body of a patient; the introducer sheath comprising a longitudinally extending lumen extending from a proximal opening thereof to a distal opening thereof, the lumen being sized to receive passage of the apparatus therethrough and out the distal opening thereof, the system further comprising a relatively compact implantable medical device, the medical device comprising a hermetically sealed housing and having an electrode mounted to the housing, the lumen of the introducer sheath being sized to receive passage of the device therethrough and out the distal opening thereto;
the apparatus comprising:
an elongate shaft extending over a length from a proximal end thereof to a distal end thereof, the shaft including a lumen extending from the proximal end to the distal end;
a dilator mounted to the distal end of the shaft, the dilator including a proximal end, a distal end, a first portion, a second portion, and a longitudinally extending lumen, the first portion extending from the proximal end of the dilator to the second portion, the second portion extending from the first portion to the distal end of the dilator, the lumen of the dilator being in fluid communication with the lumen of the shaft and including a distal opening located at the distal end of the dilator, the second portion having a decreasing taper from the first portion to the dilator distal end, the second portion including an external thread formed along the decreasing taper, and the lumen of the dilator having a nominal diameter smaller than a nominal diameter of the lumen of the shaft, the lumen of the dilator including a funnel-shaped entry, and the dilator lumen extending from the entry thereof to the distal opening thereof.

2. A system according to claim 1 wherein the thread is a non-cutting thread.

3. A system according to claim 1 wherein the first portion has an increasing taper from a first outer diameter, in proximity to the dilator proximal end, to a larger second outer diameter in proximity to the second portion.

4. A system according to claim 3 wherein the first portion of the apparatus dilator is configured to expand to, and contract from, the larger second outer diameter.

5. A system according to claim 4, further comprising a spreading member configured to slide within the dilator first portion.

6. The system of claim 3, wherein the larger second outer diameter of the dilator is greater than two times a nominal outer diameter of the shaft.

7. A system according to claim 1 further comprising an elongate flexible wire slidably engageable within the lumens of the shaft and dilator, the wire including a piercing distal tip.

8. A system according to claim 7 wherein the wire comprises a distal segment having a pre-formed J-shape and extending proximally from the piercing distal tip, the distal segment being deformable to extend lengthwise within the lumens of the shaft and dilator.

9. A system according to claim 7, wherein the apparatus further comprises an insertion stop tethered to the proximal end of the shaft of the apparatus, the insertion stop being configured to be alternately fitted around and removed from a proximal portion of the elongate flexible wire so that, when the stop is fitted around the proximal portion of the elongate flexible wire, the stop prevents the wire from sliding distally within the lumens of the shaft of the apparatus and the dilator, and, when the stop is removed, the wire is free to slide distally within the lumens of the shaft of the apparatus and of the dilator.

* * * * *